(12) United States Patent
Morgan et al.

(10) Patent No.: US 6,290,500 B1
(45) Date of Patent: Sep. 18, 2001

(54) DENTAL IMPLANT SYSTEM AND METHOD

(75) Inventors: Vincent J Morgan, Boston, MA (US); Thomas D Driskell, Westerville, OH (US)

(73) Assignee: Diro, Inc., Boston, MA (US)

( * ) Notice: Subject to any disclaimer, the term of this patent is extended or adjusted under 35 U.S.C. 154(b) by 0 days.

(21) Appl. No.: 09/581,063

(22) PCT Filed: Dec. 8, 1998

(86) PCT No.: PCT/US98/26148

§ 371 Date: Jun. 7, 2000

§ 102(e) Date: Jun. 7, 2000

(87) PCT Pub. No.: WO99/29255

PCT Pub. Date: Jun. 17, 1999

Related U.S. Application Data
(60) Provisional application No. 60/069,042, filed on Dec. 10, 1997.

(51) Int. Cl.[7] ........................................ A61C 8/00

(52) U.S. Cl. ............................................. 433/173

(58) Field of Search ........................... 433/172, 173, 433/174, 213

(56) References Cited

U.S. PATENT DOCUMENTS

| | | | | |
|---|---|---|---|---|
| 4,738,623 | * | 4/1988 | Driskell | 433/173 |
| 5,368,483 | * | 11/1994 | Sutter et al. | 433/173 |
| 5,527,182 | * | 6/1996 | Willoughby | 433/172 |
| 5,533,898 | * | 7/1996 | Mena | 433/173 |
| 5,662,476 | * | 9/1997 | Ingber et al. | 433/213 |
| 5,681,167 | * | 10/1997 | Lazarof | 433/174 |
| 5,810,590 | * | 9/1998 | Fried et al. | 433/172 |
| 5,904,483 | * | 5/1999 | Wade | 433/173 |

* cited by examiner

*Primary Examiner*—Ralph A. Lewis
(74) *Attorney, Agent, or Firm*—John A. Huag

(57) ABSTRACT

An abutment has a central portion between a post portion receivable in a dental implant and a head portion having a selected configuration. A shelf extending from the head portion outwardly to the central portion forms an angle alpha between approximately 0 and 30 degrees with an imaginary plane perpendicular to a longitudinal axis of the head portion to form a confluent joint with a crown of various emergence profiles thereon. A crown is fabricated, in certain embodiments, utilizing a sleeve having a negative image closely matching that of the selected head portion configuration. The finished crown is attached to the abutment, as by cement, polished and then inserted into the osteotomy site, angularly adjusted and locked in place using a seating device made by means of a seating jig.

11 Claims, 5 Drawing Sheets

DENTAL IMPLANT SYSTEM AND METHOD

This application is a 371 of PCT/U.S. 98/26148 filed Dec. 8, 1998 which claims benefit of provisional application Ser. No. 60/069,042 filed Dec. 10, 1997.

FIELD OF THE INVENTION

This invention relates generally to restorative dentistry and other medical procedures and more particularly to surgical implementation in the mouth of a patient and to prosthesis systems and methods used with such prosthesis systems.

BACKGROUND OF THE INVENTION

The natural teeth of an individual may be lost as a result of dental disease or trauma, making it desirable to replace such teeth with one or more prosthetic devices. An example of a prosthetic device is the dental implant which is surgically positioned within the mandibular or maxillary alveolar bone.

One type of dental implant has a first implant member for placement in an osteotomy site in the alveolar bone of a patient. Following healing, a head member, commonly called an abutment, is mounted in or on the first implant member and a tooth simulating prosthesis or crown is then mounted on the abutment. A successful system of this type is disclosed in U.S. Pat. No. 4,738,623. In that patent, a first implant or root member having a first or outer end formed with a female socket circumscribed by a shoulder and having a suitable anchoring means, such as outwardly extending fins, is placed in an osteotomy site or implant receiving cavity formed in the alveolar bone with suitable surgical instruments and techniques. The first implant member is inserted into the cavity with the upper portion of the member a selected distance below the opening of the cavity, that is, below the crest of the bone, e.g., two or three millimeters. A healing plug is inserted into a female socket of the first implant member and particles of a natural and/or synthetic bone growth stimulating grafting material are then packed within the cavity around the shoulder of the implant member and the wound is then closed.

Following healing, the dentist accesses and removes the plug and replaces it with an abutment. The abutment has a male portion received within the female socket and an intermediate, outer generally hemispherical surface portion which may extend through the surface of the gingiva and preferably through the surface of the crest of the bone which may have been previously reamed to form a complimentary configuration when forming the cavity. A prosthetic device can then be attached to the abutment forming a smooth continuous surface with the hemispherical surface portion of the abutment with the interface between the prosthetic device and the abutment being supragingival or, for best aesthetics, subgingival, that is, being covered by the gingival tissue. Fabrication of the prosthetic device typically involves making an impression, generally a full arch impression, and pouring a model forming, inter alia, a positive replica, or die, of the abutment head. A laboratory technician then burnishes platinum foil over the die which then serves as a core on which a prosthesis is built. Upon completion and firing of the prosthesis, the platinum is scratched away. Although this procedure has been acceptable, the efficacy of the result is dependent upon the skill of the technician and is highly labor intensive and time consuming. Alternatively, the technician could fabricate the prosthesis by a lost wax technique utilizing a central core of metal, usually a gold palladium alloy, onto which porcelain powders are added and fused in a firing oven. Still other techniques for prosthesis fabrication include the use of implant and abutment analogs, acrylics or composite resins. However, such methods are also highly labor intensive and time consuming.

SUMMARY OF THE INVENTION

It is an object of the invention to provide an implant system and method which minimizes laboratory procedures and concomitant expenses and time delays. Another object of the invention is the provision of an improved implant system and method in which consistent accuracy of the component parts, as well as the implant as a whole, is enhanced. Another object of the invention is the provision of a system and method for overcoming the above noted prior art limitations.

Briefly stated, a first embodiment of the invention comprises an abutment having a central portion between a post portion and a head portion, the post portion being receivable in the bore of a dental implant and the central portion being formed with a smoothly curved, convex outer surface extending from a relatively large periphery progressively down to a smaller periphery which joins the post portion. The head portion has a smaller outer periphery than that of the relatively large periphery of the central portion with a shelf formed between the base of the head portion and the central portion which forms an angle with a plane perpendicular to the longitudinal axis of the head portion within a range of approximately 0–30 degrees to facilitate the forming of a confluent joint with a prosthesis received on the head portion which is compatible with a human body, i.e., one which the body will not try to reject. The shelf slopes downwardly toward the post portion end with respect to a direction going radially outwardly from the longitudinal axis. More preferably, the angle is approximately 15 degrees. The provision of the angled shoulder permits the use of a prosthesis having a matching shoulder at the entrance to a head receiving cavity and having any one of various emergence profiles, that is, the interface of the prosthesis and the abutment can be on the shelf either flush with or inboard of the outer periphery thereof and still be compatible with the human body. Generally, the curved surface of the central portion of the abutment is generally spherical however it can also be of other smoothly curved configurations, such as ellipsoidal. Preferably, the implant is formed with a bore having a self-holding taper of less than 5 degrees and the post is formed with a matching self-holding taper. However, if desired, the bore and post could be threaded or the post could have no taper and be attached to the implant by cement or the like.

According to another feature of the invention, an integrated crowned abutment is formed by providing a sleeve of suitable material, such as porcelain, metal, resin or the like, having an internal head seat with a negative image closely matching that of a head portion of an abutment having a selected configuration so that the sleeve can be fitted precisely onto such a head portion. The sleeve is placed on the head portion of a temporary abutment having the selected configuration and having a post removably inserted in the bore of an implant positioned in an osteotomy site. An impression of moldable material is taken of the removable abutment and the area adjacent to the osteotomy site. The impression is removed from the patient's mouth with the sleeve remaining in the impression. A transfer abutment having a head portion with the same selected configuration is placed within the sleeve and the transfer abutment is inserted in an implant analog. Molding material is then poured into the impression to form a model or replica of the area adjacent to the osteotomy site with the implant analog locked in the model. The model is removed from the impression and the sleeve is removed from the impression and positioned on the transfer abutment in the model. A prosthesis is then built on the sleeve by adding suitable material such as porcelain, metal, resin and the like, and shaping the material within the available space between teeth or prostheses contiguous with and opposing the osteotomy site. The prosthesis is then attached to a permanent abutment having a head portion with the selected configuration by any suitable means, such as cementing, clipping, frictionally engaging as with a self-holding taper, or the like, to form an integrated crowned abutment. The integrated crowned abutment can be polished extraorally to remove extraneous cement when cement is used as the means of attachment and then the finished abutment can be inserted into the implant with the angular position being adjustable to any desired orientation and then locked in place. Preferably, the implant is provided with a bore having a self-holding taper of less than 5 degrees and the post of the abutment with a matching self-holding taper so that attachment is obtained by tapping the abutment into the implant with a selected force in a manner to be described. It will be understood, however, that it is within the purview of the invention to employ posts with no taper which can be cemented into the implant.

When using the self-holding attachment system a special jig is provided for ensuring that the locking force is imparted to the integrated crowned abutment by a force which is essentially collinear with the longitudinal axis of the post portion and in a way that will not mar the surface of the crown portion. The jig comprises a telescoping two part generally U-shaped frame having a seating cup in one leg of the frame with a post receiving orifice formed through the center of the seating cup, and a depression formed in a second leg of the frame extending below the plane in which the bottom surface of the second leg lies and aligned with the longitudinal axis of the orifice and the seating cup. The post of an integrated crowned abutment is placed through the orifice and the curved portion of the central portion of the abutment is seated in the seating cup. Suitable parting material, such as Vaseline or Saran wrap, is placed on the crown portion of the integrated crowned abutment to prevent adhesion of resin, such as epoxy, to be injected thereabout. The vertical position of the second end of the frame member is adjusted and doughy epoxy or other resin is placed between the integrated crowned abutment and the second leg of the frame including the portion extending below the plane in which the bottom surface of the leg lies. After the resin cures and hardens the frame is removed and the seating device is trimmed of flash and the like leaving a crown portion replicated bottom surface which will be aligned with the longitudinal axis of the post of the integrated crowned abutment when the seating device is placed on the crown. In use, the integrated crowned abutment is placed in the implant and the angular orientation is adjusted as desired either before or after the seating device is placed on the crown portion. Force is then imparted through the indentation in the epoxy which is aligned with the longitudinal axis of the post to ensure that the imparted force is collinear therewith.

According to a modified embodiment, a prefabricated crown element may be selected for placement on the head of the removable abutment, either with or without the use of a sleeve core. A cavity is provided, or is formed, in the prefabricated element and adapted to receive the head portion of an abutment, or the sleeve as described above, and the outer configuration is adapted to fit between contiguous and opposing teeth or prostheses relative to the osteotomy site to form a finished crown. The finished crown is then attached to an abutment having a self-holding tapered post extraorally to form an integrated crowned abutment for subsequent insertion into an implant having a matching self-holding taper positioned within an osteotomy site. The integrated crowned abutment is polished extraorally and inserted into the implant and its angular position adjusted and finally it is locked in place.

Additional objects and features of the invention will be set forth in part in the description which follows and in part will be obvious from the description. The objects and advantages of the invention may be realized and attained by means of the instrumentality's, combinations and methods particularly pointed out in the appended claims.

BRIEF DESCRIPTION OF THE DRAWINGS

The accompanying drawings, which are incorporated in and constitute a part of the specification, illustrate preferred embodiments of the invention and, together with the description, serve to explain the objects, advantages and principles of the invention. In the drawings.

DETAILED DESCRIPTION OF THE PREFERRED EMBODIMENTS

Figure 1:
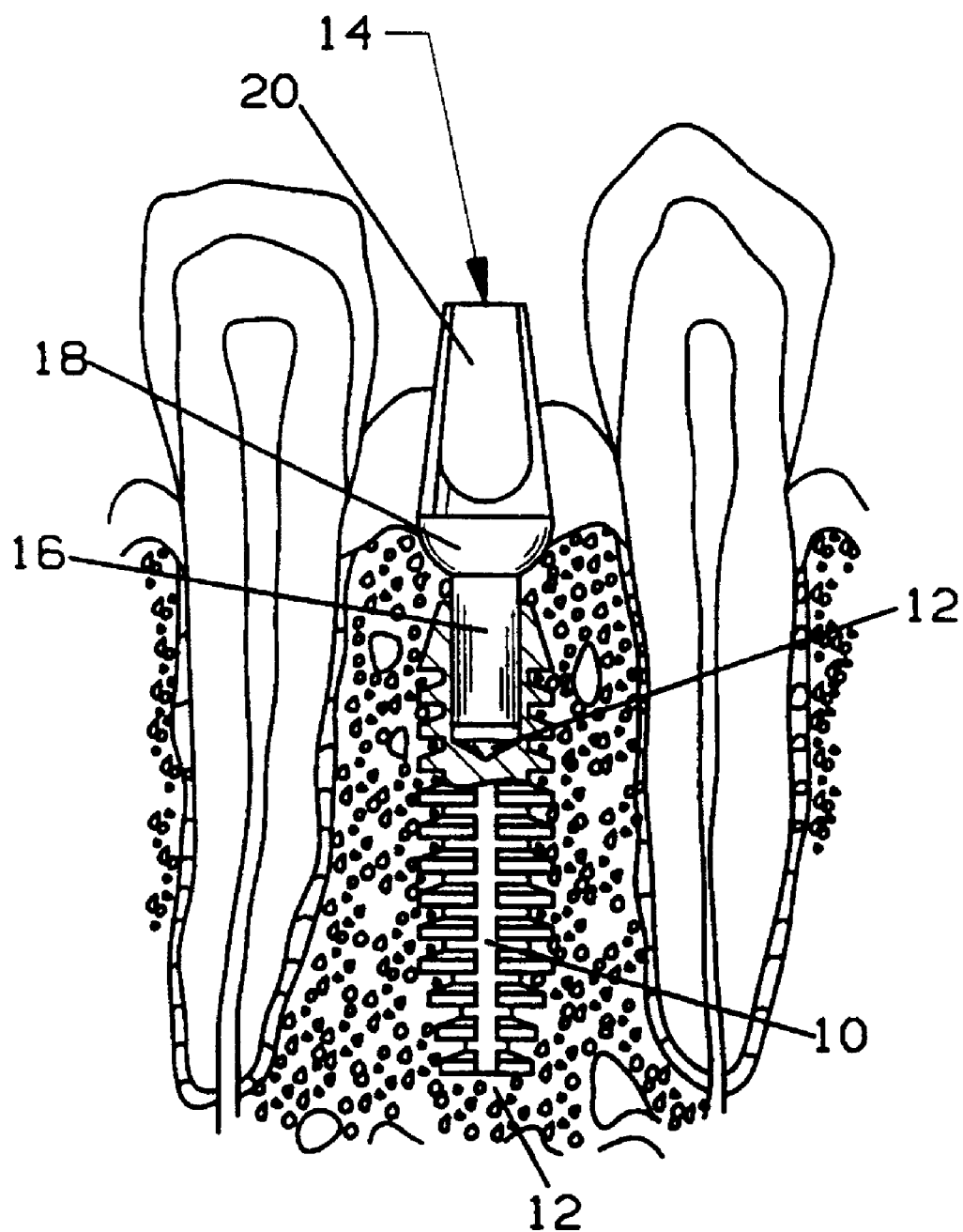
FIG. 1 is a broken away cross-sectional front elevational view of a jaw showing an abutment positioned in an implant in an osteotomy site along with contiguous teeth in accordance with the teaching of U.S. Pat. No. 4,738,623.

FIG. 1 shows a prior art system comprising an implant 10 disposed in an osteotomy site in the jaw of a patient. Implant 10 has a bore 12 formed with a self-holding taper and mounts therein an abutment 14 having a post portion 16 formed with a matching self-holding taper so that the abutment can be locked in place by tapping the abutment along the longitudinal axis of the post portion with at least a selected force. Abutment 14 has a central portion or base 18 formed with a smooth curved outer surface configuration and a head portion 20 which serves to mount a prosthesis thereon. Further details can be obtained by reference to U.S. Pat. No. 4,738,623, referenced above, the subject matter of which is incorporated herein by this reference.

As mentioned above, a crown or other prosthesis is typically fabricated by a relatively labor intensive and time consuming process involving the burnishing of platinum foil on the head of an abutment which is then built upon and shaped to fit within the space available between contiguous teeth, as shown in FIG. 1, or prostheses, and the opposing teeth or prostheses (not shown). After completion of the prosthesis the foil has to be carefully removed, as by scraping, before the prosthesis can be permanently attached to the abutment mounted in the implant. If cement is used in attaching the abutment, care must be exercised to avoid having extraneous cement on the outer surface which would irritate the gingiva.

According to an embodiment of the invention, fabrication of a prosthesis is greatly simplified by first forming the crown utilizing an abutment analog and then integrating the crown and a permanent abutment so that the prosthesis can be finished and polished extraorally. This facilitates the subgingival placement of the cement interface since there will be no flash or excess cement to irritate the gingiva tissues. The finished integrated crowned abutment, preferably having a post portion with a self-holding taper, is then inserted into the implant, its angular orientation is adjusted as desired and then it is tapped into locking engagement in the implant as a single unit utilizing a customized seating device to be described infra.

Figure 2:
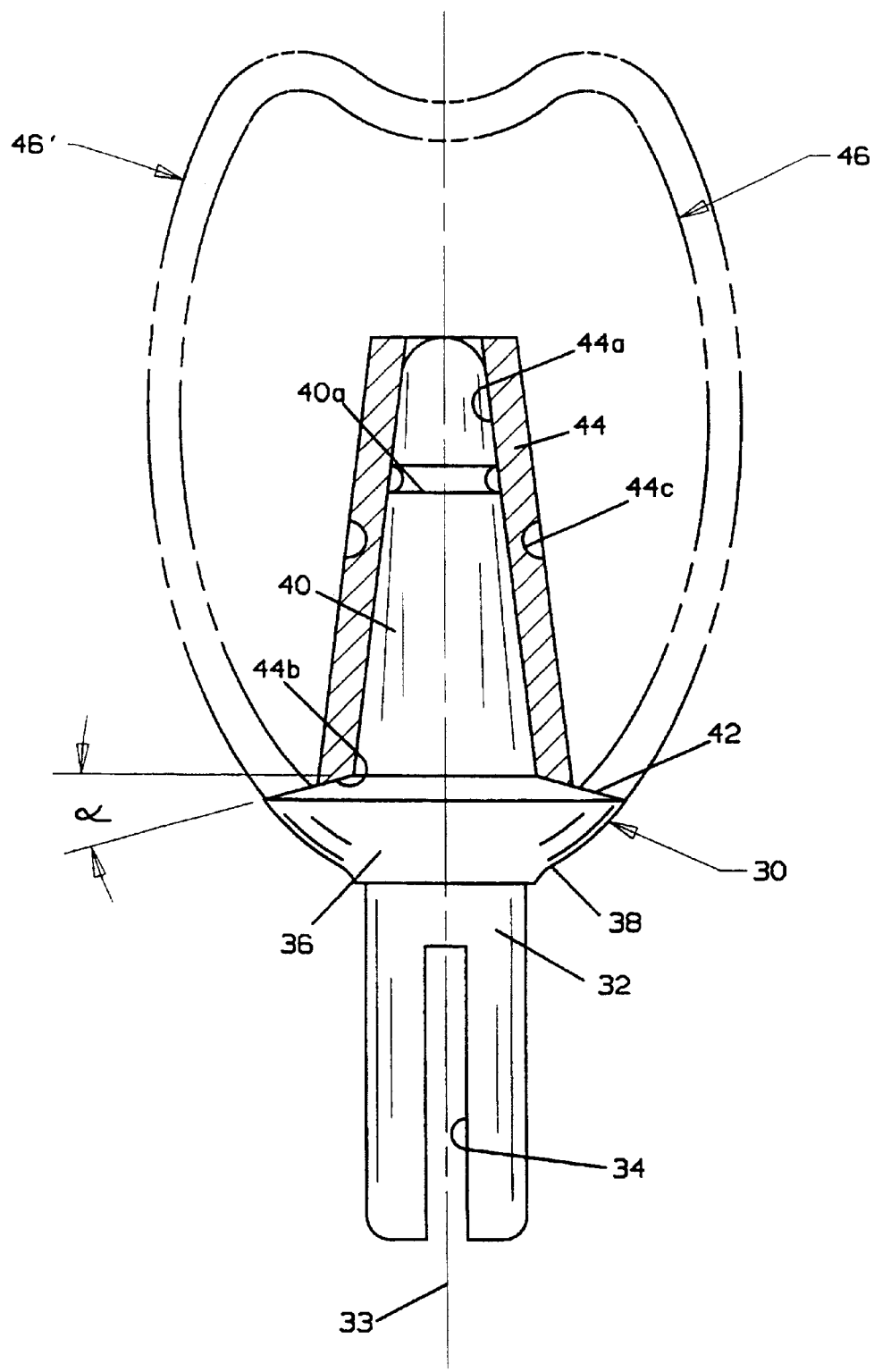
FIG. 2 is an elevational view of a temporary abutment having a sleeve core placed thereon for the fabrication of a crown made in accordance with the invention.

With reference to FIG. 2 an abutment analog 30 has a post portion 32, a generally cylindrical portion with a longitudinal axis 33, formed with a longitudinally extending slot 34 so that the post can be removably received in the bore of an implant having a self-holding taper. Abutment analog 30 has a central or base portion 36 formed with a smooth, convex, outer surface configuration 38, such as spherical, ellipsoidal or the like. A head portion 40 having a selected configuration, such as frusto-conical, extends along a longitudinal axis, in the embodiment shown axis 33, from central portion 36 on a side removed from post 32 and with the larger end of the frusto-conical configuration disposed at the central portion. Head portion 40 is preferably formed with retention means such as annular groove 40a, vertically extending serrations to prevent relative rotation (not shown), a flat (not shown), or the like. A shelf 42 extends from the junction of head 40 with central portion 36 out to the outer configuration 38. Shelf 42 preferably forms an angle alpha with an imaginary plane perpendicular to the longitudinal axis of head portion 40 in the range of approximately 0–30 degrees, and more preferably approximately 15 degrees, for a purpose to be discussed below.

After an implant, such as implant 10 of FIG. 1, has been inserted into an osteotomy site, or after it has been allowed to heal for a certain period of time, it is uncovered and a removable abutment analog, or, if desired, a permanent abutment is placed into the newly uncovered implant along with a sleeve core member 44 having an internal head seat 44a being a negative image of and closely matching that of head portion 40 and preferably formed with a retention means such as annular groove 44c on its outer periphery for a purpose to be described. An impression using conventional moldable material is taken of the area adjacent to the osteotomy site along the alveolar crest with sleeve 44 remaining in the impression with the aid of retention means 44c. An abutment analog or transfer abutment having a head with the same selected configuration is then placed within the sleeve and a slotted post of the abutment analog is inserted into an implant analog and then a positive model is made of the outer surface of the sleeve and the adjacent area with the implant locked in the model. A prosthesis is then built on the sleeve by adding and shaping the prosthesis material within the available space between teeth and/or prostheses contiguous with and opposing the osteotomy site. Prosthesis material can be any suitable material such as porcelain, metal, resin or the like.

Figure 3:
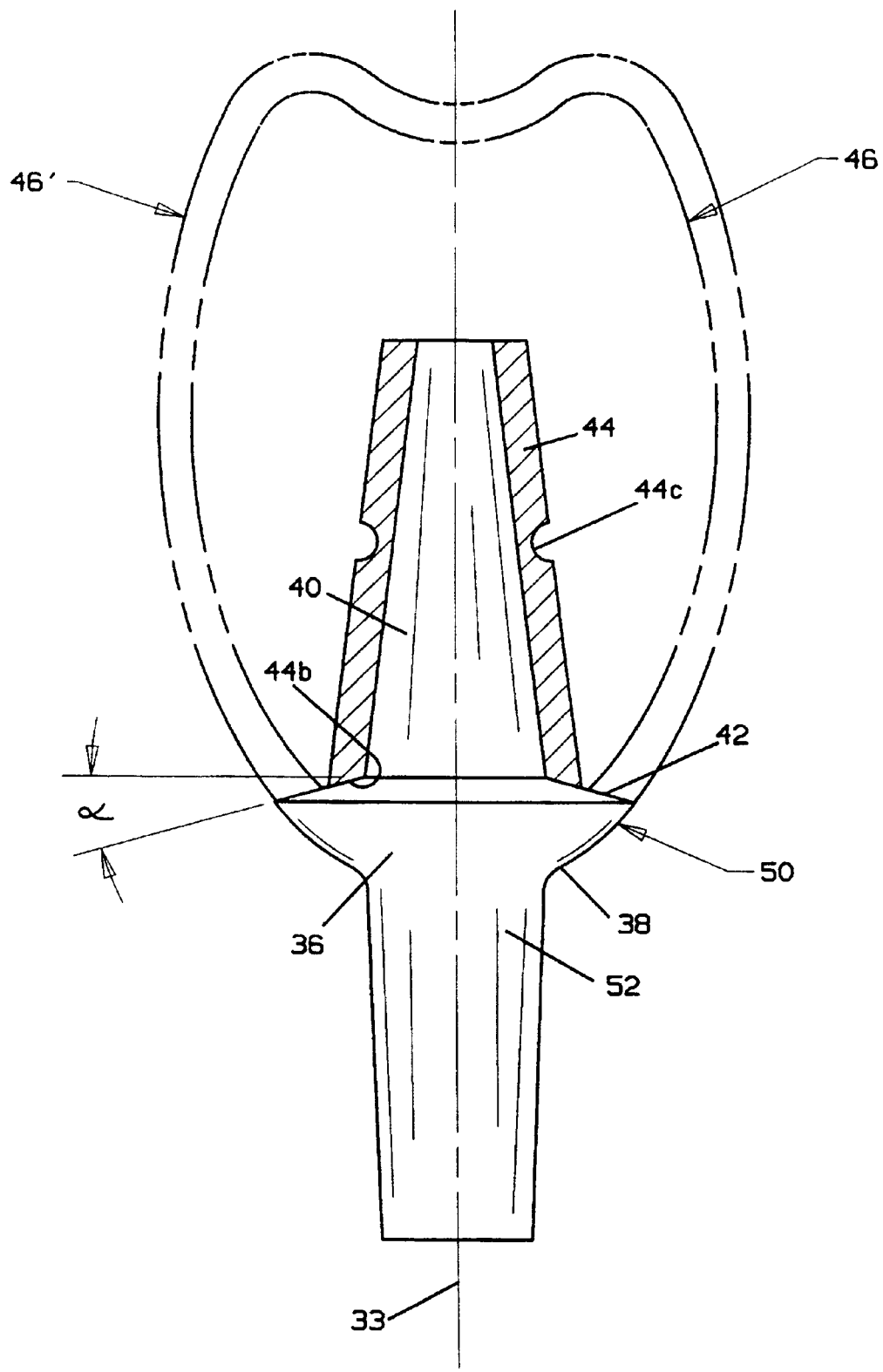
FIG. 3 is a view similar to FIG. 2 showing an abutment with the FIG. 2 sleeve core and crown portion, shown in dashed lines, comprising an integrated crowned abutment made in accordance with the invention.
Figure 3A:
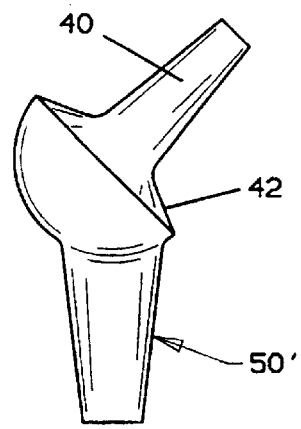
FIG. 3a is an elevational view, in reduced scale, of a modified abutment useful with the invention.

When the building and shaping has been completed prosthesis 46 is removed from abutment analog 30 and is then attached to permanent abutment 50 (FIG. 3), having the identical head portion configuration, by any suitable means, such as cementing, clipping, welding, frictional engaging, or the like, to provide an integrated crowned abutment. The integrated crowned abutment is then polished to ensure a smooth outer surface and, if the crown was attached by cement, to remove any extraneous cement material. Post 52 of abutment 50 is preferably formed with a self-holding taper of less than 5 degrees and diameter matching that of the bore of the implant with which it is intended to be used. The post portion of the finished integrated crowned abutment can then be inserted into the bore of the implant disposed in the osteotomy site and the angular orientation adjusted as desired by use of a customized acrylic jig or indexing alignment device fabricated on the laboratory model so that the crown is properly positioned within the available space and then locked in place. It will be appreciated that abutments having angled heads relative to the post, as indicated by abutment 50' in FIG. 3a, can be employed in practicing the invention. Further, although a self-holding taper is preferred for post 52, other configurations could be used, e.g., cylindrical with no taper, and could be attached to the implant by means of cement or the like.

Shelf 42 forms an angle alpha (FIG. 2) of from approximately 0–30 degrees with an imaginary plane perpendicular to the longitudinal axis of the head portion as noted above. This feature enables the use of crowns having various emergence profiles as noted by 46 and 46' shown in dashed lines in FIGS. 2 and 3. This results in a confluent joint between crown 46, 46' and either the shelf 42 or outer surface 38 of the abutment which is compatible with the human body, that is, the body will not react negatively to the presence of a step between the crown and the abutment as long as the step forms an angle alpha, as defined.

It should be noted that the end surface 44b of sleeve 44 is preferably formed having a matching angle to that of shelf 42 to provide a closely conforming mating surface.

In accordance with another embodiment of the invention, a prefabricated crown element or blank may be used with abutment 50 in fabricating an integrated crowned abutment. A blank crown having the particular desired characteristics of color and general configuration of the desired simulated tooth is selected and a head receiving cavity is then formed in the crown blank, if not already provided. The blank crown is then placed on the head portion of an abutment analog having the same head portion configuration with the abutment analog positioned in a model analog of the type described above and then material is added to, removed from and the crown blank is otherwise shaped to fit in the space between contiguous and opposing teeth and/or prostheses relative to the osteotomy site to form a finished crown. The finished crown is then attached extraorally to an abutment and, after suitable polishing, is inserted into the implant positioned within the osteotomy site. Alternatively, the fabricated crown could be attached to the permanently seated abutment intraorally by cement, friction or chemical bonding.

Figure 5:
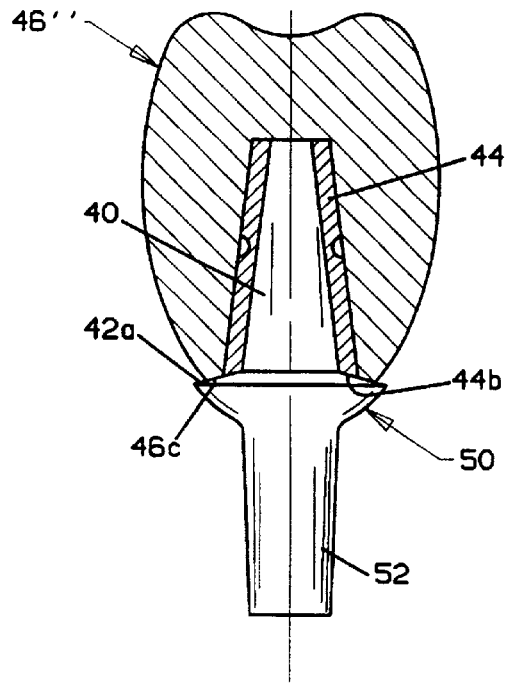
FIGS. 5 and 6 are elevational views, partly in cross-section, of an integrated crowned abutment fabricated with and without a sleeve core, respectively.
Figure 6:
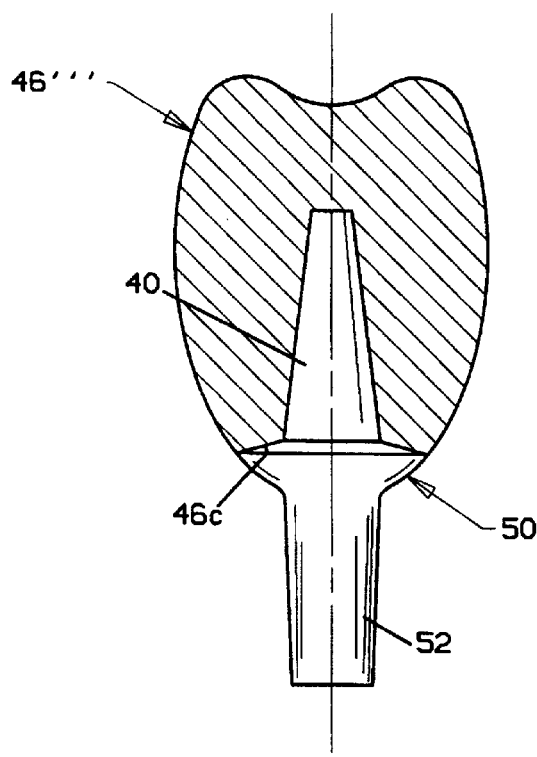

An integrated crowned abutment, made in accordance with the invention, having a sleeve core 44 is shown in FIG. 5 in which a crown 46" is attached to abutment 50 and in which post 52 is formed with a self-holding taper of less than 5 degrees. As shown in the drawing, crown 46" may form a slight step 42a which is compatible with the human body. An integrated crowned abutment, made in accordance with the invention, utilizing a preformed blank crown without the use of a sleeve core, which is custom fitted to abutment 50 as well as to contiguous and opposing teeth, is shown as crown 46''' in FIG. 6. The crowns formed in accordance with FIGS. 5 and 6 both have an end surface 46c having an angle which matches that of shelf 42.

Figure 4:
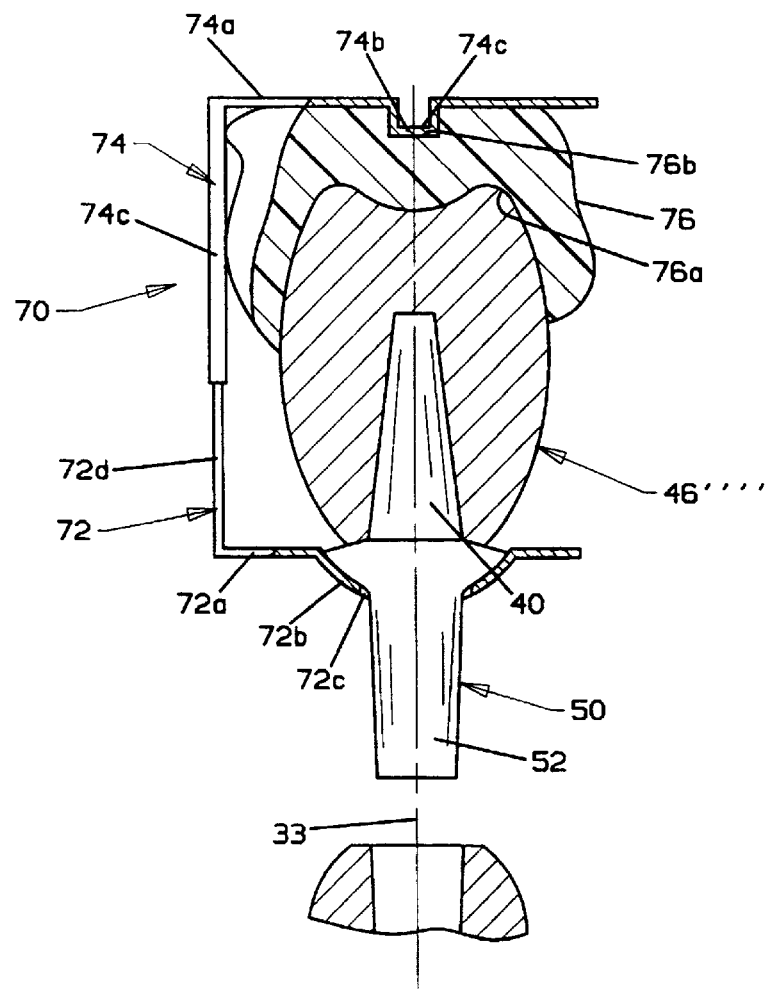
FIG. 4 is an elevational view of a seating jig used with an integrated crowned abutment having a self-holding taper.

Completed integrated crowned abutments having self-holding tapers on their post portions are locked in place by being tapped into the implant with at least a given minimum force. However, it is important that the prosthetic crown restoration not be damaged during this procedure. Such integrated crowned abutments may be installed using an alignment and indexing jig arrangement shown in FIG. 4. A generally U-shaped, telescoping, two part frame 70 is shown comprising a first L-shaped part 72 having a leg 72a formed with a cupped seat 72b having a concave configuration matching that of the outer convex surface configuration 38 of the base or central portion 36 of abutment 50 and having a post receiving orifice 72c, or other suitable opening, such as a fork, formed in the center of seat 72b. Second L-shaped part 74 has a leg 74a formed with an indentation 74b aligned with the longitudinal axis of orifice 72c and cupped seat 72b which is collinear with longitudinal axis 33 of the post 52 when the post is received in the cupped receptor. Second part 74 has a tubular second leg 74d which telescopically receives leg 72d. Preferably, a release agent such as Vaseline jelly or Saran wrap is placed over the surface of the crown portion to avoid sticking of epoxy to be discussed. Frame part 74 is then placed over crown portion 46'''' and a suitable doughy epoxy is packed into the space between leg 74a and the crown portion 46'''' including the protruding portion 74c of leg 74a opposing indentation 74b and allowed to cure into a hardened state. Frame part 74 is then removed and the integrated crown abutment and seating device 76 is removed from frame part 72. The seating device is timed of any excess flash so as not to interfere with adjacent teeth or implants in seating the integrated crowned abutment. Seating device 76, as formed, has a bottom surface 74a replicating the top surface of crown 46'''' and a top surface having an indentation 76b formed by protrusion 74c which will be aligned with the longitudinal axis of the post portion of the integrated crowned abutment when seating device 76 is received on the integrated crowned abutment.

The integrated crowned abutment can then be inserted into an implant with the seating device 76, the angular orientation of the abutment adjusted as desired along with the seating device which conforms to the outer surface configurations of the crown portion and is movable therewith, and then by using a conventional seating instrument which fits into the indentation 76b and a conventional mallet, a locking force can be delivered which will automatically be directed along the longitudinal axis 33 of the post portion and without damaging or marring the crown portion.

Seating device 76, along with abutment shelf 42, as described above, makes practical the extraoral fabrication of integrated crowned abutments.

A method for fabricating a prosthesis such as a crown, utilizing a sleeve core 44 comprises placing an abutment analog 30, that is, an analog which is removably receivable within a self-holding tapered bore of an implant, into the bore of an implant positioned within an osteotomy site. The head portion of the abutment analog is formed with a selected configuration. A sleeve core formed of suitable material having an internal head portion seat which is a negative image closely matching the selected head portion configuration of the abutment analog is placed on the head portion of the abutment analog. An impression using conventional moldable material is taken of at least the area adjacent to the osteotomy site along the alveolar crest with the sleeve remaining in the impression. An abutment analog serving as a transfer analog, having the same selected head portion configuration, is placed within the sleeve and the abutment analog is inserted into the implant A model is then made by pouring conventional dental stone material into the impression and, after hardening, is separated from the impression. The sleeve is removed from the impression and positioned on the abutment analog in the model and then the crown portion is built, for example by conventional techniques and shaped to fit within the available space between teeth contiguous with and opposing the osteotomy site.

The registration or removal of the removably receivable abutment can be accomplished at the time of implant surgery, i.e., the first stage, or after osseointegration of the implant, i.e., the uncovery or second stage surgery. If done at the first stage then the finished crown could be fabricated during the healing time and completely ready at the uncovery stage thereby resulting in time convenience for the patient as well as the clinician.

When the crown is completed it is then attached to an abutment having the same selected head portion configuration using any suitable attachment mechanism. The integrated crowned abutment is placed in jig 70 and a seating device is fabricated. After trimming of excess flash, and after polishing, the finished integrated crowned abutment is inserted into the implant in the osteotomy site and seating device 76 is positioned on the crown, the angular orientation of the prosthesis is adjusted as desired and then it is locked in place.

As noted supra, if desired, a preformed crown blank may also be utilized either with or without a sleeve core in forming an integrated crowned abutment in accordance with the invention, however, the sleeve core not only facilitates the subgingival placement of the cement interface as noted above, it also can minimize the need for angular abutments, or reduce the angularity thereof, since the trajectory through the sleeve core could accommodate different angulations of the prosthesis. An elliptical sleeve core, for example, would enhance the aesthetic and function particularly of anterior teeth. Different trajectories of the orifice in the sleeve core would accommodate the need for different alignment angulations of the crown relative to the implant. This is particularly the case in the buccal-lingual (front to back) direction. The side to side or mesio-distal direction would also be accommodated by the angulation of the abutment. The use of the sleeve having the negative image of head portion 40 obviates the labor intensive platinum burnishing process without sacrificing precision fitting. The sleeve can be formed of any suitable material by molding, machining or any other suitable means which will replicate the image of the head.

In view of the above, it will be seen that an abutment sleeve comprised of ceramic material attachable to a titanium alloy abutment can provide for an aesthetic tooth color material as an integral part of the abutment on which a conventional prosthesis can be cemented with the tooth colored material being subgingival even if the prosthesis/abutment interface is supragingival. Although the sleeve is shown with an open top end it will be understood that it could have a closed top end as well. Further, if desired, an opening in the side wall of the sleeve could be provided to accommodate direct contact of the metal abutment for seating purposes. Although not shown, a seating depression could be provided in the top surface of integrated crown abutment, if desired.

Although the invention has been described with regard to specific preferred embodiments thereof, variations and modifications will become apparent to those skilled in the art. It is therefore, the intention that the appended claims be interpreted as broadly as possible in view of the prior art to include all such variations and modifications.

What is claimed:

1. An abutment and crown for use with an implant having a first end and a second end and a longitudinal axis passing through the first end, the implant having a bore formed through the first end and extending along the longitudinal axis, the abutment comprising a central portion between a post portion and a head portion, the post portion having a longitudinal axis and being receivable in the bore of the dental implant, the central portion formed with a smoothly curved outer surface extending from a relatively large diameter progressively down to a smaller diameter where the center portion joins the post portion, the head portion having a selected outer configuration and having a longitudinal axis and having a smaller outer periphery than the periphery of the relatively large diameter of the central portion, a shelf being formed between the head portion and the central portion, the shelf forming a selected angle with a plane perpendicular to the longitudinal axis of the head portion to facilitate forming of a joint with a crown received on the head portion compatible with a human body, the crown having any one of various emergence profiles and comprising an internal sleeve having a head seat with a configuration closely matching the selected outer configuration of the head portion of the abutment, the crown having an outer portion attached to the sleeve, the outer portion of the crown having a selected outer configuration, the outer portion of the crown and the sleeve each having a lower surface formed with an angle matching that of the shelf of the abutment, the lower surface of the outer portion of the crown and the sleeve each conforming to and received on the shelf of the abutment.

2. An abutment according to claim 1 in which the curved surface of the abutment is generally convex, particularly compatible with mucosal tissue.

3. An abutment according to claim 1 in which the bore of the implant is formed with a locking taper and the post portion of the abutment is formed with a matching locking taper for receipt in the bore of the implant.

4. An abutment according to claim 1 in which the selected angle of the shelf is approximately 15 degrees.

5. An abutment according to claim 1 in which the selected angle of the shelf is within the range of approximately 5–25 degrees.

6. An abutment according to claim 1 in which the selected angle of the shelf is within the range of approximately 0–30 degrees.

7. The method of installing a crown in an implant having a bore formed with a locking taper positioned within an osteotomy site of an individual comprising the steps of taking an abutment having a head portion and a post portion, the post portion formed with a locking taper and being lockably receivable within the bore of the implant, the abutment fixing and shaping a tooth simulating crown to the head portion to form an integrated crowned abutment to fit within the confines of teeth contiguous to the osteotomy site bu placing a sleeve having an interior seating surface on the head of an abutment having an outer surface configuration which closely matches the seating surface of the sleeve and the sleeve having a lower surface received on the shelf and building up the crown by placing and shaping crown material on the sleeve with a surface of the crown material received on the shelf, inserting the post portion of the integrated abutment into the bore of the implant and adjusting the angular position of the post to a selected orientation, and tapping the integrated crowned abutment into locking engagement in the bore of the implant.

8. The method according to claim 7 in which the tooth simulating crown is fixed to the head portion by cement and after fixing the crown to the head portion further comprising the step of polishing the integrated crowned abutment to remove any extraneous cement to ensure a smooth outer surface configuration.

9. A jig for use with locking an integrated crowned abutment to an implant positioned within an osteotomy site of an individual, the integrated crowned abutment having a post portion with a longitudinal axis formed with a self-holding taper, the implant having a bore formed with a matching self-holding taper, the abutment having a curved base portion surrounding the post portion, comprising a frame having first and second end portions, the first end portion having a cupped seat with a post receiving opening formed centrally therethrough, the cupped seat having a surface configuration matching that of the curved base surface of the abutment, the frame having an indentation formed at the second end aligned with the post receiving opening, the frame adapted to receive an integrated crowned abutment having a post portion with the post portion received through the opening and the curved base surface received in the cupped seat and with the a top surface of the ingtegrated crowned abutment spaced from the second end portion of the frame and disposed between the first and second end portions spaced between opposite distal sides of the crown forming a chamber whereby spongy epoxy can be placed in the chamber to form a seating member which, after hardening, can be removed from the frame and placed on the crown positioned in an implant so that a locking force can be imparted to the integrated crowned abutment through the indentation of the seating member in a direction essentially collinear with the longitudinal axis of the bore.

10. A jig according to claim 9 in which the end portions of the frame are removably joined together by telescoping interconnecting members.

11. A seating device for use in applying a seating force to an integrated crowned abutment having a post portion with a longitudinal axis and with a self-holding taper for receipt in an implant bore having a matching self-holding taper, the integrated crowned abutment having a top crown surface portion comprising a body of molded material having a top portion formed with a force receiving indentation therein and a bottom surface contoured to fit the top crown surface portion of the abutment with the indentation aligned with the longitudinal axis of the post portion.

* * * * *